(12) United States Patent
Hancock et al.

(10) Patent No.: US 8,628,912 B2
(45) Date of Patent: Jan. 14, 2014

(54) BIOMARKERS FOR DIABETES, OBESITY, AND/OR HYPERTENSION

(75) Inventors: William S. Hancock, Brookline, MA (US); Marina Hincapie, Framingham, MA (US); M. K. Disni R. Dayarathna, Polgasowita (LK)

(73) Assignee: Northeastern University, Boston, MA (US)

( * ) Notice: Subject to any disclaimer, the term of this patent is extended or adjusted under 35 U.S.C. 154(b) by 615 days.

(21) Appl. No.: 12/667,456

(22) PCT Filed: Jul. 3, 2008

(86) PCT No.: PCT/US2008/069145
§ 371 (c)(1),
(2), (4) Date: Dec. 14, 2010

(87) PCT Pub. No.: WO2009/006568
PCT Pub. Date: Jan. 8, 2009

(65) Prior Publication Data
US 2011/0097757 A1    Apr. 28, 2011

Related U.S. Application Data

(60) Provisional application No. 60/958,125, filed on Jul. 3, 2007.

(51) Int. Cl.
*A01N 1/02* (2006.01)
(52) U.S. Cl.
USPC .......................................................... 435/2
(58) Field of Classification Search
USPC .......................................................... 435/2
See application file for complete search history.

(56) References Cited

U.S. PATENT DOCUMENTS

| | | |
|---|---|---|
| 2006/0070954 A1 | 4/2006 | Martosella et al. |
| 2006/0141528 A1 | 6/2006 | Aebersold et al. |
| 2007/0099242 A1 | 5/2007 | Heinecke et al. |

FOREIGN PATENT DOCUMENTS

WO    WO-2007044860 A2    4/2007

OTHER PUBLICATIONS

Hirano et al. "VLDL-apolipoprotein C1 is associated with increased VLDL and IDL concentrations in diabetic nephropathy", Therapeutic Research, 2000, 21(11):2622-2625.*
Dayarathna, M.K.D.R. et al., "A two step fractionation approach for plasma proteomics using immunodepletion of abundant proteins and multi-lectin affinity chromatography: Application to the analysis of obesity, diabetes, and hypertension diseases," J. Sep. Sci., vol. 31: 1156-1166 (2008).
Bren, N. D. et al., "Quantification of Human Plasma Apolipoproteins C-I, C-II, and C-III by Radioimmunoassays," Mayo Clinic Proceedings, vol. 68(7): 657-664 (1993).
Zolotarjova, N. et al., "Differences among techniques for high-abundant protein depletion," Proteomics, vol. 5: 3304-3313 (2005).
Gutman, Y. and Benzakein, F., "Antidiuretic Hormone and Renin in Rats with Diabetes Insipidus," Eur. J. Pharmacology, vol. 28: 114-118 (1974).
Shen, Z. et al., "Sepsis Plasma Protein Profiling with Immunodepletion, Three-Dimensional Liquid Chromatography Tandem Mass Spectrometry, and Spectrum Counting," J. Proteome Research, vol. 5: 3154-3160 (2006).
Yang, Z. and Hancock, W.S. "Approach to the comprehensive analysis of glycoproteins isolated from human serum using a multi-lectin affinity column," J. Chromatography, vol. 1053(1-2): 79-88 (Oct. 12, 2004).
Extended European Search Report issued for European Appl. No. 08781338.2, issued dated Mar. 17, 2011 (15 pages).
Anderson, et al., "The Human Plasma Proteome," Mol. Cell Proteomics, vol. 1(11): 845-867 (2002).
Anderson, "Candidate-based proteomics in the search for biomarkers of cardiovascular disease," J. Physiol., vol. 563(1): 23-60 (2005).
Martosella, et al., "Reversed-Phase High Performance Liquid Chromatographic Prefractionation of Immunodepleted Human Serum Proteins to Enhance Mass Spectrometry Identification of Lower-Abundant Proteins," J. Proteome Res., vol. 4: 1522-1537 (2005).
Govorukhina, et al., "Sample preparation of human serum for the analysis of tumor markers, Comparison of different approahces for albumin and Y-globulin depletion," J. Chromatogr. A., vol. 1009, 171-178 (2003).
Ogata, et al., "Evaluation of Protein Depletion Methods for the Analysis of Total-Phospho- and Glycoproteins in Lumbar Cerebrospinal Fluid," J. Proteome Res., vol. 4: 837-845 (2005).
Bjorhall, et al., "Comparison of different depletion strategies for improved resolution in proteomic analysis of human serum samples," Proteomics, vol. 5: 307-317 (2005).
Brand, et al., "Die Rolle des Angiotensinogengens fur die essentielle Hypertonie," Herz., vol. 25: 15-25 (2000).
Ailhaud, et al., "Angiotensinogen, angiotensin II and adipose tissue development," Int. J. Obes. Relat. Metab. Disord., vol. 24: S33-35 (2000).
Jong, et al., "In the Absence of the Low Density Lipoprotein Receptor, Human Apolipoprotein C1 Overexpression in Transgenic Mice Inhibits the Hepatic Uptake of Very Low Density Lipoproteins via a Receptor-assocaited Protein Sensitive Pathway," J. Clin. Invest., vol. 98: 2259-2267 (1996).
Muurling, et al., "Overexpression of APOC1 in *obob* mice leads to hepatic steatosis and severe hepatic insulin resistance," J. Lip. Res., vol. 45: 9-16 (2004).
Sharon et al., "History of lectins: from hemagglutinins to biological recognition molecules," Glycobiology, vol. 14: 53R-62R (2004).
Yang et al., "Isolation and Characterization of cDNA Clones Encoding Jacalin Isolectins," J. Biol. Chem., vol. 268: 5905-5910 (1993).
Wickremesekera et al., "Loss of Insulin Resistance after Roux-en-Y Gastric Bypass Surgery: A Time Course Study," Obesity Surgery, vol. 15: 474-481 (2005).

* cited by examiner

*Primary Examiner* — Bin Shen
(74) *Attorney, Agent, or Firm* — Wilmer Cutler Pickering Hale and Dorr LLP

(57) ABSTRACT

Methods of identifying subjects having, or at risk of developing, diabetes, obesity, and/or hypertension are disclosed, as well as methods of identifying biomarkers for diabetes, obesity, and/or hypertension, and biomarkers identified by such methods.

15 Claims, 3 Drawing Sheets

BIOMARKERS FOR DIABETES, OBESITY, AND/OR HYPERTENSION

CROSS-REFERENCE TO RELATED APPLICATIONS

This application claims the benefit of priority to U.S. Provisional Application No. 60/958,125, filed Jul. 3, 2007, the contents of which are incorporated by reference herein in their entirety.

FIELD OF THE INVENTION

The invention is in the field of medical screening and diagnosis.

BACKGROUND OF THE INVENTION

Human blood plasma is the most complex human-derived proteome. At the same time, plasma is a valuable informative proteome for medical diagnosis. The attraction of plasma for disease diagnosis lies in two characteristics: the ease by which it can be safely obtained and the fact that it comprehensively samples the human phenotype (Anderson, et al., Mol. Cell Proteomics (2002) 1.11:845-867).

Approximately half of the total protein mass in plasma is accounted by one protein (albumin), while the top ten proteins together make up 90% of the total (Anderson, J. Physiol. (2005) 563.1:23-60). This enormous dynamic range (nearly 10 orders of magnitude between the high abundance and very low abundance proteins) is currently outside the range of available technologies in proteomics.

SUMMARY OF THE INVENTION

The invention is based, at least in part, on the discovery that proteins present in plasma at low concentrations can be used as biomarkers for diabetes, obesity, and/or hypertension. This discovery was exploited to develop the invention, which, in one aspect, features a method of identifying a subject having, or at risk of developing, diabetes, obesity, and/or hypertension. The method includes the steps of determining the level of a biomarker (i) in a test biological sample obtained from the subject, and (ii) in a control biological sample of like tissue derivation from a control subject not having, or at risk of developing, diabetes, obesity, and/or hypertension; and comparing the level of the biomarker in the test sample and in the control sample; a different level of the biomarker in the test sample relative to the control sample being indicative that the subject has, or is at risk of developing, diabetes, obesity, and/or hypertension.

In some embodiments, a level of the biomarker in the test sample that is increased relative to the control sample is indicative that that subject has, or is at risk of developing, diabetes, obesity, and/or hypertension. In other embodiments, a level of the biomarker in the test sample that is decreased relative to the control sample is indicative that that subject has, or is at risk of developing, diabetes, obesity, and/or hypertension.

In some embodiments, the biomarker is one or more of actin alpha skeletal protein, alpha-2-antiplasmin, alpha-2-HS-glycoprotein, angiotensinogen, apolipoprotein AII, apolipoprotein AIV, apolipoprotein B100, apolipoprotein CI, apolipoprotein CII, apolipoprotein CIII, apolipoprotein D, apolipoprotein E, apolipoprotein-L1, apolipoprotein M, beta-2-glycoprotein I, carboxypeptidase B2, complement C1q subcomponent B chain, complement C1r subcomponent, complement C1s, complement C2, complement C5, complement component C7, complement component C8 alpha chain, complement component C8 beta chain, complement component C8 gamma chain, complement factor B, complement factor H-related protein 1, complement factor H-related protein 2, complement factor I, haptoglobin-related protein, insulin-like growth factor binding protein, kininogen-1, lumican, N-acetylmuramoyl-L-alanine amidase, plasma protease C1 inhibitor, plasma retinol-binding protein, plasminogen, platelet basic protein, serotransferrin, serum amyloid A-4 protein, serum amyloid P-component, serum paraoxonase/arylesterase 1, tetranectin, thyroxin binding globulin, Vitamin D-binding protein, or zinc-alpha-2-glycoprotein.

In certain embodiments, the test biological sample is a test plasma sample and the control biological sample is a control plasma sample. In other embodiments, the test biological sample is a test serum sample and the control biological sample is a control serum sample.

In some embodiments, determining the level of the biomarker includes measuring the protein level and/or the RNA level of the biomarker. In some embodiments, the RNA is mRNA.

In other embodiments, determining the level of the biomarker in the test sample and in the control sample includes removing from the samples proteins present at high levels. In one embodiment, the method includes the step of removing high abundance proteins from the test biological sample, resulting in a depleted test biological sample, and removing high abundance proteins from the control biological sample, resulting in a depleted control biological sample. In some embodiments, the high abundance proteins are removed using immuno-depletion. In some embodiments, the high abundance proteins albumin, IgG, IgA, transferrin, antitrypsin, and/or haptoglobin are removed. In some embodiments, immuno-depleting the samples includes using a multiple affinity removal system.

In some embodiments, the method further includes separating components of the depleted biological samples. In particular embodiments, the method includes separating the depleted test biological sample into at least a first fraction including glycosylated polypeptides and at least a second fraction including non-glycosylated polypeptides, and separating the depleted control biological sample into at least a third fraction including glycosylated polypeptides and at least a fourth fraction including non-glycosylated polypeptides. In some embodiments, the depleted biological samples are separated using chromatography. In one embodiment, a multi-lectin column is used.

In yet other embodiments, the method further includes subjecting the fractions to digestion. In one embodiment, the glycosylated polypeptides in the fractions are digested. In another embodiment, the non-glycosylated polypeptides in the fractions are digested. In particular embodiments, the method includes digesting with trypsin the non-glycosylated polypeptides in the second fraction, resulting in a test tryptic digest, and digesting with trypsin the non-glycosylated polypeptides in the fourth fraction, resulting in a control tryptic digest. In another embodiment, the method includes digesting with trypsin the glycosylated polypeptides in the first fraction, resulting in a test tryptic digest, and digesting with trypsin the glycosylated polypeptides in the third fraction, resulting in a control tryptic digest.

In other embodiments, the method further includes separating the components of the tryptic digests. In one embodiment, the components of the tryptic digests are separated using chromatography. In some embodiments, the components of the tryptic digests are separated using two dimensional chromatography or liquid chromatography-mass spectrometry (LC/MS). In one embodiment, the method includes subjecting to LC/MS the test tryptic digest, resulting in a test polypeptide profile, and subjecting to LC/MS the control tryptic digest, resulting in a control polypeptide profile. In some embodiments, the LC/MS includes reversed phase chromatography.

In another aspect, the disclosure features a method of determining the level of a biomarker in a test plasma sample relative to a control plasma sample. The method includes the steps of obtaining a test plasma sample from a test subject and a control plasma sample from a control subject; immuno-depleting albumin, IgG, IgA, transferrin, antitrypsin, and haptoglobin from the test plasma sample, resulting in a depleted test plasma sample, and immuno-depleting albumin, IgG, IgA, transferrin, antitrypsin, and haptoglobin from the control plasma sample, resulting in a depleted control plasma sample; and separating the depleted test plasma sample into a first fraction including glycosylated polypeptides and a second fraction including non-glycosylated polypeptides, and separating the depleted control plasma sample into a third fraction including glycosylated polypeptides and a fourth fraction including non-glycosylated polypeptides.

In some embodiments, the method further includes digesting with trypsin the non-glycosylated polypeptides in the second fraction, resulting in a test tryptic digest, and digesting with trypsin the non-glycosylated polypeptides in the fourth fraction, resulting in a control tryptic digest. In other embodiments, the method alternatively includes digesting with trypsin the glycosylated polypeptides in the first fraction, resulting in a test tryptic digest, and digesting with trypsin the glycosylated polypeptides in the third fraction, resulting in a control tryptic digest. In yet other embodiments, the method includes digesting with trypsin the non-glycosylated polypeptides and the glycosylated polypeptides in the fractions.

In some embodiments, the method further includes subjecting to LC/MS the test tryptic digest, resulting in a test polypeptide profile, and subjecting to LC/MS the control tryptic digest, resulting in a control polypeptide profile; and comparing the level of the biomarker in the test polypeptide profile to the level of the biomarker in the control polypeptide profile.

In some embodiments, the biomarker is one or more of actin alpha skeletal protein, alpha-2-antiplasmin, alpha-2-HS-glycoprotein, angiotensinogen, apolipoprotein AII, apolipoprotein AIV, apolipoprotein B100, apolipoprotein CI, apolipoprotein CII, apolipoprotein CIII, apolipoprotein D, apolipoprotein E, apolipoprotein-L1, apolipoprotein M, beta-2-glycoprotein I, carboxypeptidase B2, complement C1q subcomponent B chain, complement C1r subcomponent, complement C1s, complement C2, complement C5, complement component C7, complement component C8 alpha chain, complement component C8 beta chain, complement component C8 gamma chain, complement factor B, complement factor H-related protein 1, complement factor H-related protein 2, complement factor I, haptoglobin-related protein, insulin-like growth factor binding protein, kininogen-1, lumican, N-acetylmuramoyl-L-alanine amidase, plasma protease C1 inhibitor, plasma retinol-binding protein, plasminogen, platelet basic protein, serotransferrin, serum amyloid A-4 protein, serum amyloid P-component, serum paraoxonase/arylesterase 1, tetranectin, thyroxin binding globulin, Vitamin D-binding protein, or zinc-alpha-2-glycoprotein.

In certain embodiments, immuno-depleting the samples includes a multiple affinity removal system. In other embodiments, separating the depleted samples includes using a multi-lectin column. In yet other embodiments, the LC/MS includes reversed phase chromatography.

In some embodiments, a level of the biomarker in the test plasma sample that is different relative to the control plasma sample is indicative that the test subject has, or is at risk of developing, diabetes, obesity, and/or hypertension. In some embodiments, a level of the biomarker in the test plasma sample that is increased relative to the control plasma sample is indicative that the test subject has, or is at risk of developing, diabetes, obesity, and/or hypertension. In other embodiments, a level of the biomarker in the test plasma sample that is decreased relative to the control plasma sample is indicative that the test subject has, or is at risk of developing, diabetes, obesity, and/or hypertension.

In another aspect, the disclosure features a method of determining the level of a biomarker in a test serum sample relative to a control serum sample. In some embodiments, the method includes the steps of obtaining a test serum sample from a test subject and a control serum sample from a control subject; immuno-depleting albumin, IgG, IgA, transferrin, antitrypsin, and haptoglobin from the test serum sample, resulting in a depleted test serum sample, and immuno-depleting albumin, IgG, IgA, transferrin, antitrypsin, and haptoglobin from the control serum sample, resulting in a depleted control serum sample; and separating the depleted test serum sample into a first fraction including glycosylated polypeptides and a second fraction including non-glycosylated polypeptides, and separating the depleted control serum sample into a third fraction including glycosylated polypeptides and a fourth fraction including non-glycosylated polypeptides.

In some embodiments, the method further includes digesting with trypsin the non-glycosylated polypeptides in the second fraction, resulting in a test tryptic digest, and digesting with trypsin the non-glycosylated polypeptides in the fourth fraction, resulting in a control tryptic digest. In other embodiments, the method alternatively includes digesting with trypsin the glycosylated polypeptides in the first fraction, resulting in a test tryptic digest, and digesting with trypsin the glycosylated polypeptides in the third fraction, resulting in a control tryptic digest. In yet other embodiments, the method includes digesting with trypsin the non-glycosylated polypeptides and the glycosylated polypeptides in the fractions.

In some embodiments, the method further includes subjecting to LC/MS the test tryptic digest, resulting in a test polypeptide profile, and subjecting to LC/MS the control tryptic digest, resulting in a control polypeptide profile; and comparing the level of the biomarker in the test polypeptide profile to the level of the biomarker in the control polypeptide profile.

In some embodiments, the biomarker is one or more of actin alpha skeletal protein, alpha-2-antiplasmin, alpha-2-HS-glycoprotein, angiotensinogen, apolipoprotein AII, apolipoprotein AIV, apolipoprotein B100, apolipoprotein CI, apolipoprotein CII, apolipoprotein CIII, apolipoprotein D, apolipoprotein E, apolipoprotein-L1, apolipoprotein M, beta-2-glycoprotein I, carboxypeptidase B2, complement C1q subcomponent B chain, complement C1r subcomponent, complement C1s, complement C2, complement C5, complement component C7, complement component C8 alpha chain, complement component C8 beta chain, complement component C8 gamma chain, complement factor B, complement factor H-related protein 1, complement factor H-related protein 2, complement factor I, haptoglobin-related protein, insulin-like growth factor binding protein, kininogen-1, lumican, N-acetylmuramoyl-L-alanine amidase, plasma protease C1 inhibitor, plasma retinol-binding protein, plasminogen, platelet basic protein, serotransferrin, serum amyloid A-4 protein, serum amyloid P-component, serum paraoxonase/arylesterase 1, tetranectin, thyroxin binding globulin, Vitamin D-binding protein, or zinc-alpha-2-glycoprotein.

In certain embodiments, immuno-depleting the samples includes a multiple affinity removal system. In other embodiments, separating the depleted samples includes using a multi-lectin column. In yet other embodiments, the LC/MS includes reversed phase chromatography.

In some embodiments, a level of the biomarker in the test serum sample that is different relative to the control serum sample is indicative that the test subject has, or is at risk of developing, diabetes, obesity, and/or hypertension. In some embodiments, a level of the biomarker in the test serum sample that is increased relative to the control serum sample is indicative that the test subject has, or is at risk of developing, diabetes, obesity, and/or hypertension. In other embodiments, a level of the biomarker in the test serum sample that is decreased relative to the control serum sample is indicative that the test subject has, or is at risk of developing, diabetes, obesity, and/or hypertension.

In another aspect, the disclosure features a method of identifying a biomarker for diabetes, obesity, and/or hypertension. The method includes the steps of obtaining a test plasma sample from a subject having or at risk of developing diabetes, obesity, and/or hypertension; obtaining a control plasma sample from a subject not having or not at risk of developing diabetes, obesity, and/or hypertension; immuno-depleting albumin, IgG, IgA, transferrin, antitrypsin, and haptoglobin from the test sample and from the control sample, resulting in a depleted test sample and a depleted control sample; separating the depleted test sample into a first fraction including test glycosylated polypeptides and a second fraction including test non-glycosylated polypeptides; separating the depleted control sample into a third fraction including control glycosylated polypeptides and a fourth fraction including control non-glycosylated polypeptides; independently digesting the test non-glycosylated polypeptides in the second fraction and the control non-glycosylated polypeptides in the fourth fraction with trypsin, resulting in a test tryptic digest and a control tryptic digest; independently subjecting the test tryptic digest and the control tryptic to LC/MS, resulting in a test polypeptide profile and a control polypeptide profile; and comparing the test polypeptide profile and the control polypeptide profile; a polypeptide present at a level in the test polypeptide profile that is different than in the control polypeptide profile being indicative of the polypeptide as a biomarker for diabetes, obesity, and/or hypertension.

In some embodiments, a level of the biomarker in the test polypeptide profile that is increased relative to the control polypeptide profile is indicative of the polypeptide as a biomarker for diabetes, obesity, and/or hypertension. In other embodiments, a level of the biomarker in the test polypeptide profile that is decreased relative to the control polypeptide profile is indicative of the polypeptide as a biomarker for diabetes, obesity, and/or hypertension.

In some embodiments, immuno-depleting the samples includes a multiple affinity removal system. In other embodiments, separating the depleted samples includes using a multi-lectin column. In yet other embodiments, the LC/MS includes reversed phase chromatography.

In another aspect, the disclosure features a method of identifying a biomarker for diabetes, obesity, and/or hypertension. The method includes the steps of obtaining a test plasma sample from a subject having or at risk of developing diabetes, obesity, and/or hypertension; obtaining a control plasma sample from a subject not having or not at risk of developing diabetes, obesity, and/or hypertension; immuno-depleting albumin, IgG, IgA, transferrin, antitrypsin, and haptoglobin from the test sample and from the control sample, resulting in a depleted test sample and a depleted control sample; separating the depleted test sample into a first fraction including test glycosylated polypeptides and a second fraction including test non-glycosylated polypeptides; separating the depleted control sample into a third fraction including control glycosylated polypeptides and a fourth fraction including control non-glycosylated polypeptides; independently digesting the test glycosylated polypeptides in the first fraction and the control glycosylated polypeptides in the third fraction with trypsin, resulting in a test tryptic digest and a control tryptic digest; independently subjecting the test tryptic digest and the control tryptic to LC/MS, resulting in a test polypeptide profile and a control polypeptide profile; and comparing the test polypeptide profile and the control polypeptide profile; a polypeptide present at a level in the test polypeptide profile that is different than in the control polypeptide profile being indicative of the polypeptide as a biomarker for diabetes, obesity, and/or hypertension.

In some embodiments, a level of the biomarker in the test polypeptide profile that is increased relative to the control polypeptide profile is indicative of the polypeptide as a biomarker for diabetes, obesity, and/or hypertension. In other embodiments, a level of the biomarker in the test polypeptide profile that is decreased relative to the control polypeptide profile is indicative of the polypeptide as a biomarker for diabetes, obesity, and/or hypertension.

In some embodiments, immuno-depleting the samples includes a multiple affinity removal system. In other embodiments, separating the depleted samples includes using a multi-lectin column. In yet other embodiments, the LC/MS includes reversed phase chromatography.

In another aspect, the disclosure features a method of identifying a biomarker for diabetes, obesity, and/or hypertension. The method includes the steps of obtaining a test serum sample from a subject having or at risk of developing diabetes, obesity, and/or hypertension; obtaining a control serum sample from a subject not having or not at risk of developing diabetes, obesity, and/or hypertension; immuno-depleting albumin, IgG, IgA, transferrin, antitrypsin, and haptoglobin from the test sample and from the control sample, resulting in a depleted test sample and a depleted control sample; separating the depleted test sample into a first fraction including test glycosylated polypeptides and a second fraction including test non-glycosylated polypeptides; separating the depleted control sample into a third fraction including control glycosylated polypeptides and a fourth fraction including control non-glycosylated polypeptides; independently digesting the test non-glycosylated polypeptides in the second fraction and the control non-glycosylated polypeptides in the fourth fraction with trypsin, resulting in a test tryptic digest and a control tryptic digest; independently subjecting the test tryptic digest and the control tryptic to LC/MS, resulting in a test polypeptide profile and a control polypeptide profile; and comparing the test polypeptide profile and the control polypeptide profile; a polypeptide present at a level in the test polypeptide profile that is different than in the control polypeptide profile being indicative of the polypeptide as a biomarker for diabetes, obesity, and/or hypertension.

In some embodiments, a level of the biomarker in the test polypeptide profile that is increased relative to the control polypeptide profile is indicative of the polypeptide as a biomarker for diabetes, obesity, and/or hypertension. In other embodiments, a level of the biomarker in the test polypeptide profile that is decreased relative to the control polypeptide profile is indicative of the polypeptide as a biomarker for diabetes, obesity, and/or hypertension.

In some embodiments, immuno-depleting the samples includes a multiple affinity removal system. In other embodiments, separating the depleted samples includes using a multi-lectin column. In yet other embodiments, the LC/MS includes reversed phase chromatography.

In another aspect, the disclosure features a method of identifying a biomarker for diabetes, obesity, and/or hypertension. The method includes the steps of obtaining a test serum sample from a subject having or at risk of developing diabetes, obesity, and/or hypertension; obtaining a control serum sample from a subject not having or not at risk of developing diabetes, obesity, and/or hypertension; immuno-depleting albumin, IgG, IgA, transferrin, antitrypsin, and haptoglobin from the test sample and from the control sample, resulting in a depleted test sample and a depleted control sample; separating the depleted test sample into a first fraction including test glycosylated polypeptides and a second fraction including test non-glycosylated polypeptides; separating the depleted control sample into a third fraction including control glycosylated polypeptides and a fourth fraction including control non-glycosylated polypeptides; independently digesting the test glycosylated polypeptides in the first fraction and the control glycosylated polypeptides in the third fraction with trypsin, resulting in a test tryptic digest and a control tryptic digest; independently subjecting the test tryptic digest and the control tryptic to LC/MS, resulting in a test polypeptide profile and a control polypeptide profile; and comparing the test polypeptide profile and the control polypeptide profile; a polypeptide present at a level in the test polypeptide profile that is different than in the control polypeptide profile being indicative of the polypeptide as a biomarker for diabetes, obesity, and/or hypertension.

In some embodiments, a level of the biomarker in the test polypeptide profile that is increased relative to the control polypeptide profile is indicative of the polypeptide as a biomarker for diabetes, obesity, and/or hypertension. In other embodiments, a level of the biomarker in the test polypeptide profile that is decreased relative to the control polypeptide profile is indicative of the polypeptide as a biomarker for diabetes, obesity, and/or hypertension.

In some embodiments, immuno-depleting the samples includes a multiple affinity removal system. In other embodiments, separating the depleted samples includes using a multi-lectin column. In yet other embodiments, the LC/MS includes reversed phase chromatography.

In another aspect, the disclosure features a method of selecting a subject for gastric bypass surgery, the method including the steps of determining the level of a biomarker (i) in a test biological sample obtained from a candidate subject, and (ii) in a control biological sample of like tissue derivation from a control subject not having, or at risk of developing, diabetes, obesity, and/or hypertension; comparing the level of the biomarker in the test sample and in the control sample; and selecting the candidate subject as a subject for gastric bypass surgery if the level of the biomarker in the test sample is different relative to the control sample.

In some embodiments, the biomarker is one or more of actin alpha skeletal protein, alpha-2-antiplasmin, alpha-2-HS-glycoprotein, angiotensinogen, apolipoprotein AII, apolipoprotein AIV, apolipoprotein B100, apolipoprotein CI, apolipoprotein CII, apolipoprotein CIII, apolipoprotein D, apolipoprotein E, apolipoprotein-L1, apolipoprotein M, beta-2-glycoprotein I, carboxypeptidase B2, complement C1q subcomponent B chain, complement C1r subcomponent, complement C1s, complement C2, complement C5, complement component C7, complement component C8 alpha chain, complement component C8 beta chain, complement component C8 gamma chain, complement factor B, complement factor H-related protein 1, complement factor H-related protein 2, complement factor I, haptoglobin-related protein, insulin-like growth factor binding protein, kininogen-1, lumican, N-acetylmuramoyl-L-alanine amidase, plasma protease C1 inhibitor, plasma retinol-binding protein, plasminogen, platelet basic protein, serotransferrin, serum amyloid A-4 protein, serum amyloid P-component, serum paraoxonase/arylesterase 1, tetranectin, thyroxin binding globulin, Vitamin D-binding protein, or zinc-alpha-2-glycoprotein.

In certain embodiments, the test biological sample is a test plasma sample and the control biological sample is a control plasma sample. In other embodiments, the test biological sample is a test serum sample and the control biological sample is a control serum sample.

In some embodiments, determining the level of the biomarker includes measuring the protein level and/or the RNA level of the biomarker. In some embodiments, the RNA is mRNA.

In other embodiments, determining the level of the biomarker in the test sample and in the control sample includes removing from the samples proteins present at high levels. In one embodiment, the method includes the step of removing high abundance proteins from the test biological sample, resulting in a depleted test biological sample, and removing high abundance proteins from the control biological sample, resulting in a depleted control biological sample. In some embodiments, the high abundance proteins are removed using immuno-depletion. In some embodiments, the high abundance proteins albumin, IgG, IgA, transferrin, antitrypsin, and/or haptoglobin are removed. In some embodiments, immuno-depleting the samples includes using a multiple affinity removal system.

In some embodiments, the method further includes separating components of the depleted biological samples. In particular embodiments, the method includes separating the depleted test biological sample into at least a first fraction including glycosylated polypeptides and at least a second fraction including non-glycosylated polypeptides, and separating the depleted control biological sample into at least a third fraction including glycosylated polypeptides and at least a fourth fraction including non-glycosylated polypeptides. In some embodiments, the depleted biological samples are separated using chromatography. In one embodiment, a multi-lectin column is used.

In yet other embodiments, the method further includes subjecting the fractions to digestion. In one embodiment, the glycosylated polypeptides in the fractions are digested. In another embodiment, the non-glycosylated polypeptides in the fractions are digested. In particular embodiments, the method includes digesting with trypsin the non-glycosylated polypeptides in the second fraction, resulting in a test tryptic digest, and digesting with trypsin the non-glycosylated polypeptides in the fourth fraction, resulting in a control tryptic digest. In another embodiment, the method includes digesting with trypsin the glycosylated polypeptides in the first fraction, resulting in a test tryptic digest, and digesting with trypsin the glycosylated polypeptides in the third fraction, resulting in a control tryptic digest.

In other embodiments, the method further includes separating the components of the tryptic digests. In one embodiment, the components of the tryptic digests are separated using chromatography. In some embodiments, the components of the tryptic digests are separated using two dimensional chromatography or liquid chromatography-mass spectrometry (LC/MS). In one embodiment, the method includes subjecting to LC/MS the test tryptic digest, resulting in a test polypeptide profile, and subjecting to LC/MS the control tryptic digest, resulting in a control polypeptide profile. In some embodiments, the LC/MS includes reversed phase chromatography.

The following figures are presented for the purpose of illustration only, and are not intended to be limiting.

DETAILED DESCRIPTION OF THE INVENTION

Figure 1:
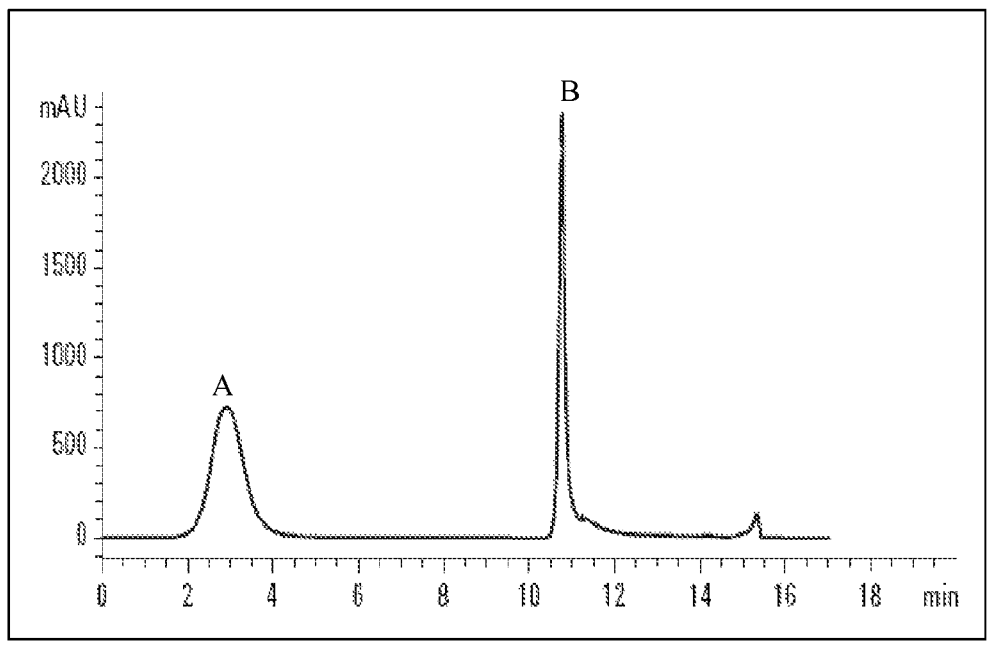
FIG. 1 is a graphic representation of a chromatogram obtained during the depletion of a plasma sample. Peak A corresponds to flow-through fraction (low & medium abundance proteins) and peak B corresponds to bound fraction (high abundance proteins).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein, including GenBank database sequences, are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DEFINITIONS

As used herein, the term "biological sample" refers to a sample obtained from an organism or from components (e.g., cells) of an organism. The sample may be of any biological tissue or fluid, for example, a sample derived from a patient. Such samples include, but are not limited to, blood, blood cells (e.g., white cells), plasma, tissue or fine needle biopsy samples, urine, peritoneal fluid, and pleural fluid, or cells there from. Biological samples may also include sections of tissues such as frozen sections taken for histological purposes.

As used herein, the term "biomarker" of a disease or condition refers to a gene or a gene product that is up- or down-regulated in a biological sample of a subject having the disease or condition relative to a biological sample from like tissue derivation, which gene or gene product is sufficiently specific to the disease or condition that it can be used, optionally with other genes or gene products, to identify or detect the disease or condition. Generally, a biomarker is a gene or a gene product that is characteristic of the disease or condition.

The term "protein" is used interchangeably herein with the terms "peptide" and "polypeptide".

As used herein, a "subject" is a mammal, e.g., a human, mouse, rat, guinea pig, dog, cat, horse, cow, pig, or non-human primate, such as a monkey, chimpanzee, baboon or rhesus.

The present disclosure relates, at least in part, to methods of identifying individuals having, or at risk of developing, diabetes, obesity, and/or hypertension. The present disclosure is based, at least in part, on the identification of proteins that are differentially expressed in diabetic, obese and/or hypertensive subjects relative to normal subjects.

Measuring Biomarkers

The methods described herein include the detection of the level of markers, e.g., to identify subjects having, or at risk of developing, diabetes, obesity, and/or hypertension. Such markers can be detected at the RNA or protein level, e.g., in samples described herein, using methods well known to those of skill in the art. Such assay methods include, but are not limited to, immunoassays, radio-immunoassays, competitive-binding assays, Western Blot analysis, ELISA assays, and immunofluorescence assays. Other assay methods include spectroscopy, such as mass spectroscopy. These markers are detected after separation from a biological sample.

Separation Techniques

To evaluate the presence of biomarkers in biological samples, e.g., plasma, the proteins in the biological samples can be separated to facilitate analysis using various separation techniques. Separation techniques include, but are not limited to, column chromatography, filtration, ultrafiltration, salt precipitation, solvent precipitation, solvent extraction, distillation, immunoprecipitation, SDS-polyacrylamide gel electrophoresis, isoelectric point electrophoresis, dialysis, and recrystallization.

For chromatography, affinity chromatography, ion-exchange chromatography, hydrophobic chromatography, gel filtration, reverse phase chromatography, adsorption chromatography, and such may be used (see, e.g., *Strategies for Protein Purification and Characterization: A Laboratory Course Manual*. Ed, Daniel R. Marshak et al., Cold Spring Harbor Laboratory Press (1996)). These chromatography procedures can also be liquid chromatography, such as HPLC and FPLC.

In some instances, the presence of biomarkers in a biological sample can be measured by optionally modifying or partially degrading the proteins in a biological sample, for example, by treating the biological sample with an appropriate protein modification enzyme before separation. Such a modification or partial degradation can be utilized when, for example, the proteins in a biological sample are not easily separated. Such protein modification enzymes include, for example, trypsin, chymotrypsin, lysylendopeptidase, protein kinase, and glucosidase.

In certain instances, multidimensional separation techniques, such as tryptic peptide fractionation using reversed phase and ion exchange LC, or protein pre-fractionation methods, like ion exchange, size exclusion, hydrophobic interaction and various affinity methods, can be used (Martosella, et al., *J. Proteome Res*. (2005) 4:1522-1537). One nonlimiting example of a pre-fractionation method includes removing high abundance proteins to reduce the dynamic range of protein levels in biological fluids to better match that of the analytical platform.

A variety of depletion methods for specific removal of high abundance proteins from bodily fluids can be used (see, e.g., Govorukhina, et al., *J. Chromatogr. A* (2003) 1009:171-178). A nonlimiting example is the multiple affinity removal system (MARS, Agilent, Palo Alto, Calif.), which utilizes an affinity column. This column can deplete albumin, IgG, IgA, transferrin, haptoglobin and antitrypsin in human plasma (Ogata, et al., *J. Proteome Res*. (2005) 4:837-845; Bjorhall, et al., *Proteomics* (2005) 5:307-317). The MARS column can deplete these proteins from 30-40 µl of plasma at a time and can be regenerated up to 200 times.

Another separation technique that can be used in the method disclosed herein involves using a combination of three lectins in the form of a multi lectin column (M-LAC). This affinity column can capture and enrich fractions, e.g., glycoprotein fractions, in plasma. In some instances, fractions can be subjected to LC-MS after tryptic digestion (Yang, et al., *J. Chromategr. A* (2004) 1053:79-88).

Methods of Diagnosis

The methods described herein can be used to identify a subject having, or at risk of developing, diabetes, obesity, and/or hypertension. The methods described herein include obtaining a biological sample from a subject having, or at risk of developing, diabetes, obesity, and/or hypertension, and a sample from a subject not having, or not at risk of developing, these conditions. The biological sample can be, e.g., urine, blood, serum, plasma, saliva, semen, a vaginal secretion, or cerebrospinal fluid. In some instances, the biological sample is a plasma sample.

Any marker described herein, or identified using a method described herein, can be used as a marker to identify a subject having, or at risk of developing, diabetes, obesity, and/or hypertension. For example, the level of one or more of the following markers can be measured: actin alpha skeletal protein, alpha-2-antiplasmin, alpha-2-HS-glycoprotein, angiotensinogen, apolipoprotein AII, apolipoprotein AIV, apolipoprotein B100, apolipoprotein CI, apolipoprotein CII, apolipoprotein CIII, apolipoprotein D, apolipoprotein E, apolipoprotein-L1, apolipoprotein M, beta-2-glycoprotein I, carboxypeptidase B2, complement C1q subcomponent B chain, complement C1r subcomponent, complement C1s, complement C2, complement C5, complement component C7, complement component C8 alpha chain, complement component C8 beta chain, complement component C8 gamma chain, complement factor B, complement factor H-related protein 1, complement factor H-related protein 2, complement factor I, haptoglobin-related protein, insulin-like growth factor binding protein, kininogen-1, lumican, N-acetylmuramoyl-L-alanine amidase, plasma protease C1 inhibitor, plasma retinol-binding protein, plasminogen, platelet basic protein, serotransferrin, serum amyloid A-4 protein, serum amyloid P-component, serum paraoxonase/arylesterase 1, tetranectin, thyroxin binding globulin, Vitamin D-binding protein, or zinc-alpha-2-glycoprotein. If the protein or RNA level of one or more of these markers is different relative to the control level, the subject can be classified as having, or at risk of developing, diabetes, obesity, and/or hypertension. The Swiss Protein Accession Numbers for the markers described herein are listed in Tables 2-7.

Angiotensinogen is associated with essential hypertension. Essential hypertension is a complex disease influenced by different genetic and environmental factors. Initial studies done on hypertensive siblings and case-control studies indicated the important role of the angiotensinogen gene for the predisposition to essential hypertension, preeclampsia and obesity-related hypertension (Brand, et al., *Herz*. (2000), 25:15-25). Adipose tissue is an important source of angiotensinogen. A local renin-angiotensinogen system (RAS) is present in human adipose tissue and may act as a distinct system from plasma RAS. In obese patients, increased secretion of angiotensinogen from adipose tissue with a resulting increase in plasma levels of angiotensin II may be a step in the development of hypertension (Ailhaud, et al., *Int. J. Obes. Relat. Metab. Disord*. (2000), 24:S33-35).

Apolipoprotein C1 overexpression is associated with decreased particulate uptake of Apo B-containing lipoproteins, which may lead to increased levels of several potentially atherogenic species, including cholesterol-enriched VLDL, IDL, and LDL (Jong, et al., *J. Clin. Invest*. (1996) 98:2259-2267). This in turn may lead to high blood pressure. The effects of Apo C1 overexpression on hepatic and peripheral insulin sensitivity have been studied in a mouse model, where obese ob/ob mice with mild over expression of Apo C1 were generated and resulted in hepatic steatosis and severe hepatic insulin resistance (Muurling, et al., *J. Lip. Res*. (2004) 45:9-16).

Once a subject is identified as having, or at risk of developing, diabetes, obesity, and/or hypertension, the subject can be treated with an appropriate therapy for the condition. Such therapies include traditional therapies known in the art, e.g., insulin therapy or gastric bypass surgery.

The invention is further illustrated by the following examples. The examples are provided for illustrative purposes only. They are not to be construed as limiting the scope or content of the invention in any way.

EXAMPLES

Example 1

Identification of Proteins Differentially Expressed in Diabetic, Obese, and/or Hypertensive Subjects Relative to Normal Subjects Protocol A. Samples and Reagents Human plasma samples were obtained from Bioreclamation Inc., (Hicksville, N.Y.) and Trypsin (sequencing grade) was purchased from Promega (Madison, Wis.). Agarose bound Concanavalin A, Jacalin and Wheat germ agglutinin lectins were obtained from Vector labs (Burlingame, Calif.). Disposable polypropylene columns were obtained from Pierce biotechnology, Inc., (Rockford, Ill.) and 5 kDa Amicon molecular weight cut off filters were purchased from Millipore (Billerica, Mass.).

Sodium phosphate, sodium chloride, ultra pure (hydroxymethyl)aminomethane hydrochloride, sodium azide, urea, glycine, guanidine hydrochloride, dithiothreitol, ammonium bicarbonate, iodoacetamide, manganese chloride tetrahydrate, calcium chloride, methyl-α-mannopyrannoside, N-acetyl-glucosamine, methyl-α-glucopyrannoside, Bovine fetuin, and galactose were purchased from Sigma-Aldrich (St. Louis, Mo.). Concentrated hydrochloric acid, trifluoroacetic acid, glacial acetic acid and HPLC grade acetonitrile were purchased from Fisher scientific (Fair lawn, N.J.), and formic acid (acid free) was purchased from MP Biochemicals, Inc., (Solon, Ohio). HPLC grade water used in all experiments was from J. T Baker (Bedford, Mass.). Discovery® BIO wide pore C18 cartridges were from (3 µm particle diameter, 4.6 mm×30 mm) Supelco (Bellefonte, Pa.).

B. Sample Preparation for Proteomic Analysis

Human plasma samples (received frozen in dry ice from Bioreclamation, Inc.) were selected from females; plasma was obtained from four groups of individuals: (1) Normal (healthy); (2) Obese; (3) Obese, Diabetic and non-Hypertensive; and (4) Obese, Diabetic and Hypertensive females. Table 1 summarizes the characteristics of the patients selected for this study and supplied by Bioreclamation Inc. Samples were randomized for proteomic analysis to protect data from any variables or biases. Two samples were processed from each of these pools and were also analyzed in duplicate at the MS level to give four measurements per pool. Each group consisted of five individuals (5 ml of plasma each) and a plasma sample pool for each of the four groups was made by combining 3 ml from each of the five individuals within a group. The remaining 2 ml of sample from each individual was stored separately at −70° C. for the analysis of individuals at a later stage.

TABLE 1

Patient[a] Characteristics

| Characteristics | Normal | Obese | Obese + Diabetic | Obese + diabetic + Hypertensive |
|---|---|---|---|---|
| 1. Gender | Female | Female | Female | Female |
| 2. Age in years (range) | 38 ± 8.51 | 36 ± 10.99 | 44 ± 10.26 | 43 ± 14.78 |
| 3. Body Mass Index | <30 kg/m$^2$ | >30 kg/m$^2$ | >30 kg/m$^2$ | >30 kg/m$^2$ |
| 4. Treatments for | | | | |
| I. Diabetes | 0% | 0% | 100% | 60% |
| II. Hypertension. | 0% | 0% | 0% | 60% |

[a] Five individual plasma samples in each group were pooled for the study

C. Depletion of Six most Abundant Proteins in Human Plasma Using the Multiple Affinity Removal Column (MARS)

Plasma was depleted of six abundant proteins using a 4.6 mm×100 mm MARS column (Agilent, Palo Alto, Calif.). The depletion was performed at room temperature (25° C.) on an Integral™ Analytical Workstation (Perseptive Biosystems, Inc. Cambridge, Mass.) by using manual injection mode. To remove any particulates, a micro filter was attached before the column. Protein elution was monitored at a wavelength of 280 nm during the chromatography fractionation process. The loading capacity of the MARS column was about 30-40 μl of human plasma. The amount of plasma processed per sample was 70 μl; two separate samples, each consisting of 35 μl, were injected onto the depletion column. These human plasma samples (35 μl) were diluted to 250 μl using binding buffer (supplied by the manufacture). An internal standard was added to each sample; 2.5 μl from 10 mg/ml solution of bovine fetuin was added to each sample. The final concentration of bovine fetuin was 10 pmol/35 μl of plasma.

The column was initially equilibrated with the binding buffer (12 ml), and the sample was loaded at a low flow rate (0.5 ml/min) for 2.5 min. The flow rate was then set at 1.0 ml/min for the remainder of the run. The unbound proteins were removed by washing the column with an additional 10 ml of binding buffer. Then the bound six high abundance proteins were released with elution buffer supplied by the manufacturer. The eluted proteins were collected and the column was immediately neutralized by adding binding buffer (10 ml). Each run cycle took 32 min of total run time.

Both depleted (flow-through fraction) and plasma abundant proteins (bound fraction) were collected and stored at −20° C. until further analysis.

The volume of the depleted fractions prepared from each sample was concentrated to 200 μl using Amicon 5 kDa molecular weight filters (Millipore, Mass.) and buffer exchanged three times (3 ml each) with a buffer containing 25 mM Tris, 0.1 M NaCl, 0.05% NaN$_3$ at pH 7.4. These samples, together with the bound fractions from the depletion step, were subjected to a Bradford protein assay using bovine serum albumin (BSA) as the standard, according to the manufacturer's instructions (Pierce, Rockford, Ill.).

D. Affinity Capture and Enrichment of Glycoproteins from Depleted Human Plasma Using Multi Lectin Affinity Chromatography (M-LAC)

Disposable polypropylene columns with 5 ml capacity (Pierce Biotechnology Inc, Rockford, Ill.) were used in this procedure. Each sample was loaded onto a new column. The M-LAC column was prepared from a stock solution of lectins. Equal amounts of a 50% slurry of agarose-bound Concanavalin A, Jacalin and Wheat germ agglutinin lectins were mixed together to obtain a total of 1 ml M-LAC column, ready for affinity capture of glycosylated plasma glycoproteins.

To the depleted human plasma samples (300 μl) were added 3 μl of a solution of 10 mM Ca$^{2+}$ and 10 mM Mn$^{2+}$ ions, just before multi-lectin affinity chromatography. The M-LAC column was equilibrated with 12 ml of binding buffer (25 mM Tris, 0.1 M sodium chloride, 1 mM calcium chloride, 1 mM manganese chloride, 0.05% sodium azide at pH 7.4). The plasma sample was loaded onto the column slowly and incubated at room temperature for 15 min. After the incubation period, unbound non-glycosylated proteins were washed with 4 ml of binding buffer and collected directly in to an Amicon 5 kDa molecular weight filter (Millipore, Mass.) containing 125 μl of 5 mM EDTA. Bound glycoproteins were then eluted with buffer (0.5 M sodium chloride, 25 mM Tris, 0.2 M methyl-α-mannopyrannoside, 0.2 M methyl-α-glucopyrannoside, 0.8 M galactose, 0.5 M N-acetyl-glucosamine, 0.05% sodium azide at pH 7.4) into another Amicon filter containing EDTA. Both fractions were concentrated to 100 μl. The filters were washed with another 100 μl solution of 10 mM Tris, pH 7.4, and aliquots of combined bound and unbound fractions were subjected to a Bradford protein assay to determine the total amount of glycoproteins and non-glycoproteins present in the samples.

E. Tryptic Digestion of Non-Glycosylated Proteins

The non-glycosylated fractions obtained from the M-LAC were concentrated to 50 μl using 5 kDa Amicon molecular weight cut off filters, and 6 M guanidine chloride (150 μl) was then added to denature the proteins. This sample was reconcentrated to 50 μl and reduced using a solution of 5 mM dithiothreitol (DTT) followed by incubation at 60° C. for 40 min. The reduced samples were brought to room temperature and alkylated by adding 15 mM iodoacetamide (1.5 μl of 0.5 M iodoacetamide) and incubated in the dark for 30 min. At the end of the incubation period, 5 μl of 0.1 M DTT was added to stop the alkylation. The samples were diluted with 200 μl of 50 mM ammonium bicarbonate solution, pH 8, and trypsin (Promega, Madison, Wis.) was added at a ratio of 1:25 (w/w). The samples were incubated at 37° C. for 18 hr. Next, additional trypsin (1:25 w/w) was added, and the samples were held at 37° C. for 2 to 4 hr to maximize protein digestion. Finally, the digestion was terminated by adding 1% formic acid gradually, until the pH was below 4.

F. Reversed Phase C18 Sample Clean-Up Before Nano LC-MS/MS Analysis

Before analyzing the digested protein samples using LC/MS, the salts present in the samples (such as guanidium hydrochloride and ammonium bicarbonate) were removed on a C18 cartridge (Bio C18, 3 μm, 4.6 mm×30 mm) Desalting was performed on a Shimadzu SPD 10A high performance liquid chromatography system (Norwell, Mass.).

The injection volume was 300 μl and a full loop injection mode was used. Both 280 and 214 nm were monitored during the desalting process. The total chromatographic procedure took 16 min.

The chromatographic column was equilibrated with a high aqueous mobile phase composition (98% of mobile phase A). After loading the sample, the salts were removed with an isocratic wash. Then the organic mobile phase was increased to 30% using 0.07% trifluoroacetic acid in acetonitrile, mobile phase B, where the peptides were eluted from the column. The peptides were collected into eppendorf tubes and the organic mobile phase was increased to 90% B to elute the partially digested or undigested proteins. The peptides eluted at 30% organic mobile phase were collected (2 ml) and concentrated to 20 μl using a LABCONCO Freeze dryer (Kansas City, Mo.) at −90° C. and stored at −70° C. until LC/MS analysis.

G. Nano LC-MS/MS Analysis

The LC/MS and LC/MS/MS experiments were performed on an Ettan MDLC system (GE Healthcare, Piscataway, N.J.) coupled to a Finnigan linear ion trap mass spectrometer (Thermoelectron, San Jose, Calif.). The capillary column used for LC/MS/MS analysis (150 mm×0.075 mm) was from New Objective (Woburn, Mass.) and slurry packed in house with 5 μm, 200 Å pore size Magic C18 stationary phase (Michrom Bioresources, Auburn, Calif.). The flow rate for sample separation was 200 nl/min. Mobile phase A was 0.1% formic acid in water and mobile phase B was 0.1% formic acid in acetonitrile. Routinely, 2.5 μl of each sample corresponding to approximately 4 μg of total proteins was injected onto the column using the MDLC autosampler. The following gradient was used for all analyses: 0% B (minimum equilibration for 30 min); followed by linear gradient to 40% B over 160 mins; then to 90% B over 20 mins; and then constant 90% B for 20 mins All separations were performed at ambient temperature. The ion transfer tube of the linear ion trap was held at 245° C.; the normalized collision energy was 35% for MS/MS. The spray voltage was set at 2.0 kV. The mass spectrometer was operated in the data dependant mode to switch automatically between MS and MS/MS acquisitions using MS acquisition software (Xcalibur 1.4, Thermo Electron, San Jose, Calif.). Each MS full scan (mass range of m/z 400 to m/z 2000) was followed by seven MS/MS scans of the seven most intense peaks. A precursor ion was excluded from further LTQ MS/MS analysis for 2 min.

H. Data Processing and Analysis

Peptides and proteins were identified by automated searching of all MS and MS/MS spectra against spectra of theoretical fragmentations of a human protein database (Swiss-Prot, uploaded in September 2005) using Sequest algorithm incorporated into the BioWorks software, Version 3.2, (Thermoelectron, San Jose, Calif.). Only the peptides resulting from tryptic cleavages were searched and two trypsin missed cleavages were allowed. Carbamidomethylation of cysteines was included in the search parameters. The Sequest results were filtered using correlation score (Xcorr) values (Xcorr 1.9, 2.2, 3.75 for singly, doubly and triply charged peptides, respectively) and validated using Protein Prophet™ software by applying a minimum 95% probability, and protein identifications were based on at least two peptides. The identified protein list was sorted again to exclude any proteins that were identified with fewer than two unique peptides. The proteins that had a difference of two fold or more (by spectral counts) (Liu, et al., *Anal. Chem.* (2004), 76:4193-4201), between the normal and the disease pools were identified. However, in some cases, a single peptide was detected for a protein within a given group, and are referred to as "singletons". Proteins identified by a single peptide were accepted only where other groups showed a significant difference in spectral counts. The proteins that came under the above category were selected for the peak area quantitation. Peak area quantitation was done manually using at least two peptides per protein. These peak areas were normalized using a peak area of a selected peptide obtained for the internal standard, bovine fetuin, which was carried through the entire analysis procedure. Normalization was performed to correct any sample losses and process variations (e.g., variations in injection volumes) that might have happened during the analysis of the sample set.

Results

The MARS column removed six abundant proteins in human plasma (albumin, immunoglobulin G, immunoglobulin A, transferrin, antitrypsin and haptoglobin) efficiently (FIG. 1). This was assessed by the number of peptides identified during the LC-MS/MS analysis of the depleted sample. After depletion of the high abundance proteins, the protein yield in the flow through fraction was 9.7% of the total proteins. 70 μl of plasma containing 3.5-4.0 mg of total protein were initially used, and at the end of the depletion step, the total protein content in the flow-through fraction was 0.35-0.4 mg.

The M-LAC column consisted of Concanavalin A (Con A), Jacalin (JAC) and Wheat Germ Agglutinin (WGA) lectins separately cross-linked to agarose beads. This combination of lectins recognizes the most common sugar residues found in human plasma: Con A, JAC and WGA recognize α-mannose, galactose, N-acetyl glucosamine and sialic acid, respectively (Sharon et al., *Glycobiology* (2004) 14:53R-62R; Yang et al., *J. Biol. Chem.* (1993) 268:5905-5910). The M-LAC column was used as a fractionation method in this approach to simplify the sample mixture into two fractions, namely glycosylated proteins and non-glycosylated proteins. The column was run under gravity conditions, and a fresh column was used for each sample. The divalent ions, $Ca^{2+}$ and $Mn^{2+}$, were added to the samples before the fractionation step to facilitate binding of plasma glycoproteins to Con A.

From the amount of total proteins loaded on to the M-LAC column, about 56% of the proteins were in the flow-through fraction. Some of the proteins in this fraction have been identified as potential glycoproteins. The tryptic digests of non-glycosylated fractions were then analyzed by LC/MS.

Figure 2:
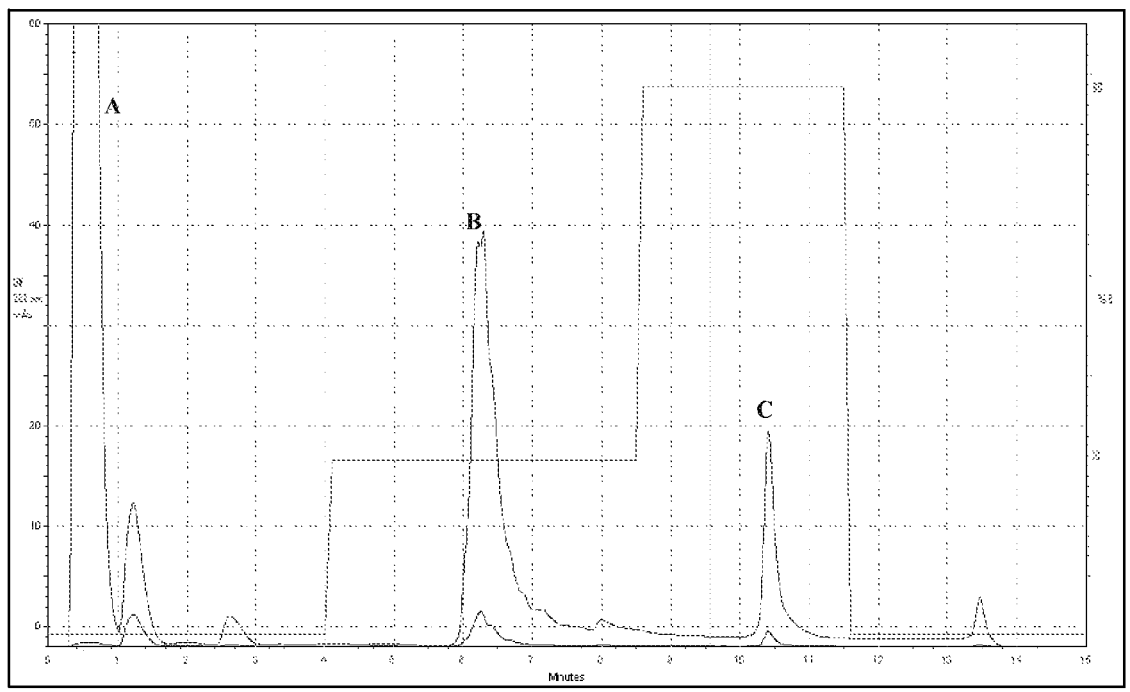
FIG. 2 is a graphic representation of a chromatogram obtained during the desalting and fractionation of a trypsin digest on a C18 column. Peak A corresponds to salts that were removed by the column, and peak B corresponds to peptides that were also separated from the undigested/partially digested proteins (peak C).

The non-glycosylated protein fraction was subjected to tryptic digestion and then "cleaned" before LC/MS analysis using a C18 column and a gradient system of organic and aqueous mobile phase as described above. This procedure separated the peptides from any undigested or partially digested proteins and removed salt. Both 280 nm and 214 nm were monitored during the desalting process (FIG. 2).

Figure 3:
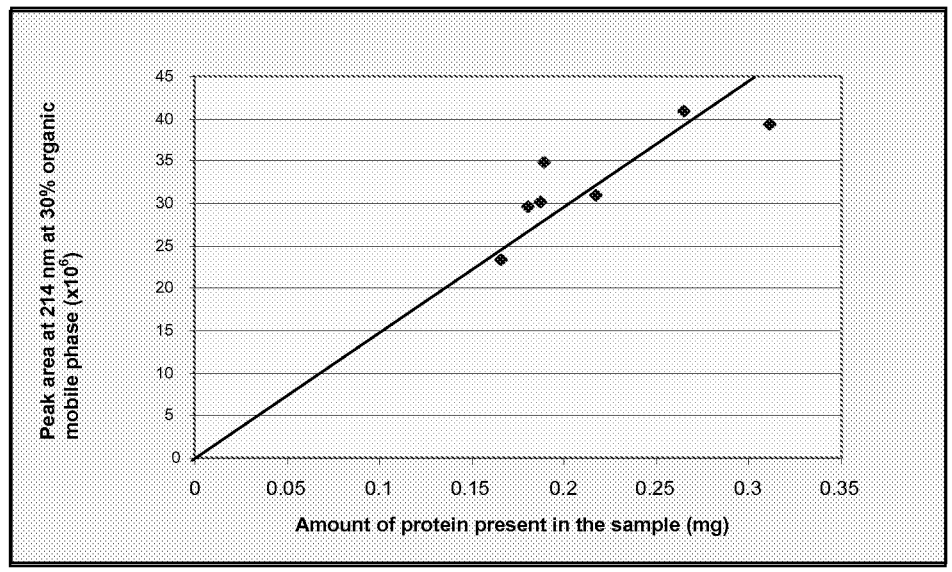
FIG. 3 is a graphic representation of the peak areas obtained at 30% organic mobile phase elution versus the amount of protein digested with trypsin.

This desalting method was further explored to better control the amount of sample loaded onto the LC-MS column. FIG. 3 shows the correlation between the peak area measured at 214 nm (at 30% organic mobile phase) against the total protein content loaded onto the desalting column (Bradford assay, before digestion). A linear correlation between the protein amount and the peak area was found. Therefore, peak area was used to normalize the amount of protein that was loaded onto the LC/MS column to control for sample losses and for variable trypsin digestions.

While the spectral count measurement were used as an initial measure of the amount of a given peptide in a sample, peak areas were used for further study of differences in protein amounts between different clinical samples. The peak area was measured in an extracted ion chromatogram at a predetermined precursor ion mass and retention time window. The retention time window that was assigned was ±0.5 min. Smoothing was also applied before integrating the peak areas to facilitate manual integration. The quantitative information obtained from one peptide was compared with data obtained from a second peptide from the same protein to ensure the accuracy of the quantitation. The peptides that were quantitated were unique for that particular protein, and at least two peptides were quantitated per protein in all the samples. In addition, a known amount of an internal standard (bovine fetuin) was spiked into the samples before the depletion step, and peak area of a selected fetuin peptide was used to normalize the sample amounts. After the peak areas of peptides of a given protein were normalized, a threshold for differential protein abundance was set at greater than two-fold change between the normal and the disease samples.

The peptide spectra obtained from the LTQ mass spectrometer were searched against tryptic peptide sequences of human protein database using the Sequest algorithm incorporated in to the BioWorks software, Version 3.2, (Thermoelectron, San Jose, Calif.). Stringent filtering criteria was used to minimize false peptide assignments, such as a minimum of 95% probability, a mass accuracy of 1.5 Da and Xcorr values of 1.9, 2.2 and 3.75 for +1, +2 and +3 charged ions, respectively. A total of 257 proteins were identified with high confidence. From the aggregated list of proteins identified in the four pools, 156 proteins were found that were identified with at least two unique peptides.

Tables 2 to 7 summarize the list of proteins identified as differentially expressed between the normal and disease groups.

TABLE 2

Proteins Upregulated in Obese Female Patients

| Swiss Protein Accession No. | Name of the protein | No of peptide sequencing events found in obese pool | | | Average no of peptide seq. Events | No of peptide sequencing events found in Normal pool | | | Average no of peptide seq. Events | Ratio of averages b/w two pools |
|---|---|---|---|---|---|---|---|---|---|---|
| | | Sample 1 | Sample 2 | Sample 3 | | Sample 1 | Sample 2 | Sample 3 | | |
| P68133 | Actin alpha skeletal protein | 4 | 5 | 0 | 3 | 0 | 0 | 0 | 0 | 3.0 |
| P06727 | Apolipoprotein A-IV precursor | 35 | 36 | 48 | 40 | 26 | 14 | 16 | 19 | 2.1 |
| P04114 | Apolipoprotein B-100 precursor | 185 | 128 | 169 | 161 | 45 | 82 | 45 | 57 | 2.8 |
| P02654 | Apolipoprotein C-I precursor | 11 | 5 | 12 | 9 | 0 | 3 | 0 | 1 | 9.3 |
| P02655 | Apolipoprotein C-II precursor | 0 | 3 | 6 | 3 | 0 | 0 | 0 | 0 | 3.0 |
| P02656 | Apolipoprotein C-III precursor | 8 | 9 | 10 | 9 | 2 | 0 | 2 | 1 | 6.8 |
| P00736 | Complement C1r subcomponent precursor | 5 | 2 | 3 | 3 | 0 | 2 | 2 | 1 | 2.5 |
| P01031 | Complement C5 precursor | 6 | 7 | 13 | 9 | 2 | 5 | 6 | 4 | 2.0 |
| P10643 | Complement component C7 precursor | 3 | 2 | 6 | 4 | 0 | 3 | 0 | 1 | 3.7 |
| P00751 | Complement factor B precursor | 135 | 62 | 94 | 97 | 55 | 37 | 56 | 49 | 2.0 |
| P36980 | Complement factor H-related protein 2 precursor | 0 | 4 | 4 | 3 | 3 | 0 | 0 | 1 | 2.7 |
| P05156 | Complement factor I precursor | 11 | 9 | 11 | 10 | 6 | 0 | 7 | 4 | 2.4 |
| P35858 | Insulin-like growth factor binding protein complex acid labile cha | 7 | 4 | 6 | 6 | 0 | 3 | 0 | 1 | 5.7 |
| P05155 | Plasma protease C1 inhibitor precursor | 7 | 5 | 8 | 7 | 0 | 4 | 2 | 2 | 3.3 |
| P27169 | Serum paraoxonase/arylesterase 1 | 5 | 5 | 8 | 6 | 0 | 4 | 0 | 1 | 4.5 |
| P25311 | Zinc-alpha-2-glycoprotein precursor | 7 | 5 | 7 | 6 | 3 | 3 | 3 | 3 | 2.1 |

TABLE 3

Proteins Downregulated in Obese Female Patients

| Swiss Protein Accession No. | Name of the protein | No of peptide sequencing events found in obese pool | | | Average no of peptide seq. Events | No of peptide sequencing events found in Normal pool | | | Average no of peptide seq. Events | Ratio of averages b/w two pools |
|---|---|---|---|---|---|---|---|---|---|---|
| | | Sample 1 | Sample 2 | Sample 3 | | Sample 1 | Sample 2 | Sample 3 | | |
| P08697 | Alpha-2-antiplasmin precursor | 0 | 0 | 0 | 0 | 3 | 4 | 0 | 2 | 0.0 |
| O95445 | Apolipoprotein M | 2 | 0 | 5 | 2 | 7 | 3 | 6 | 5 | 0.4 |
| Q96IY4 | Carboxypeptidase B2 precursor | 2 | 0 | 0 | 1 | 2 | 0 | 2 | 1 | 0.5 |
| P09871 | Complement C1s subcomponent precursor s | 3 | 6 | 0 | 3 | 9 | 4 | 6 | 6 | 0.5 |
| P00747 | Plasminogen precursor | 2 | 0 | 3 | 2 | 8 | 6 | 7 | 7 | 0.2 |
| P02775 | Platelet basic protein precursor | 2 | 0 | 0 | 1 | 0 | 3 | 3 | 2 | 0.3 |

TABLE 4

Proteins Upregulated in Obese and Diabetic Female Patients

| Swiss Protein Accession No. | Name of the protein | No of peptide sequencing events found in diabetic pool | | | Average no of peptide seq. Events | No of peptide sequencing events found in Normal pool | | | Average no of peptide seq. Events | Ratio of averages b/w two pools |
|---|---|---|---|---|---|---|---|---|---|---|
| | | Sample 1 | Sample 2 | Sample 3 | | Sample 1 | Sample 2 | Sample 3 | | |
| P68133 | Actin alpha skeletal protein | 4 | 5 | 3 | 4 | 0 | 0 | 0 | 0 | 4.0 |
| P04114 | Apolipoprotein B-100 precursor | 154 | 104 | 159 | 139 | 45 | 82 | 45 | 57 | 2.4 |
| P02654 | Apolipoprotein C-I precursor | 13 | 7 | 8 | 9 | 0 | 3 | 0 | 1 | 9.3 |
| P02656 | Apolipoprotein C-III precursor | 9 | 3 | 4 | 5 | 2 | 0 | 2 | 1 | 4.0 |
| P02746 | Complement C1q subcomponent, B chain precursor | 2 | 0 | 3 | 2 | 2 | 0 | 0 | 1 | 2.5 |
| P06681 | Complement C2 precursor | 0 | 4 | 8 | 4 | 0 | 2 | 0 | 1 | 6.0 |
| P01031 | Complement C5 precursor | 14 | 4 | 12 | 10 | 2 | 5 | 6 | 4 | 2.3 |
| P10643 | Complement component C7 precursor | 5 | 3 | 6 | 5 | 0 | 3 | 0 | 1 | 4.7 |
| P35858 | Insulin-like growth factor binding protein complex acid labile cha | 5 | 3 | 7 | 5 | 0 | 3 | 0 | 1 | 5.0 |
| P05155 | Plasma protease C1 inhibitor precursor (C1 Inh) (C1Inh) Total | 5 | 4 | 8 | 6 | 0 | 4 | 2 | 2 | 2.8 |
| P27169 | Serum paraoxonase/arylesterase 1 | 3 | 0 | 5 | 3 | 0 | 4 | 0 | 1 | 2.0 |
| P25311 | Thyroxin binding globulin precursor | 4 | 2 | 0 | 2 | 0 | 0 | 0 | 0 | 2.0 |

TABLE 5

Proteins Downregulated in Obese and Diabetic Female Patients

| Swiss Protein Accession No. | Name of the protein | No of peptide sequencing events found in diabetic pool | | | Average no of peptide seq. Events | No of peptide sequencing events found in Normal pool | | | Average no of peptide seq. Events | Ratio of averages b/w two pools |
|---|---|---|---|---|---|---|---|---|---|---|
| | | Sample 1 | Sample 2 | Sample 3 | | Sample 1 | Sample 2 | Sample 3 | | |
| P02765 | Alpha-2-HS-glycoprotein precursor | 9 | 5 | 3 | 6 | 21 | 20 | 17 | 19 | 0.3 |
| P02749 | Beta-2-glycoprotein I precursor | 30 | 22 | 27 | 26 | 64 | 63 | 59 | 62 | 0.4 |
| Q03591 | Complement factor H-related protein 1 precursor | 0 | 0 | 0 | 0 | 3 | 7 | 0 | 3 | 0.0 |
| P01042 | Kininogen-1 precursor | 20 | 7 | 11 | 13 | 29 | 19 | 28 | 25 | 0.5 |
| Q96PD5 | N-acetylmuramoyl-L-alanine amidase precursor | 2 | 0 | 0 | 1 | 4 | 8 | 4 | 5 | 0.1 |
| P02753 | Plasma retinol-binding protein precursor | 18 | 12 | 10 | 13 | 40 | 16 | 26 | 27 | 0.5 |
| P00747 | Plasminogen precursor | 4 | 3 | 0 | 2 | 8 | 6 | 7 | 7 | 0.3 |
| P02775 | Platelet basic protein precursor | 0 | 0 | 3 | 1 | 0 | 3 | 3 | 2 | 0.5 |
| P35542 | Serum amyloid A-4 protein precursor | 5 | 4 | 0 | 3 | 13 | 4 | 10 | 9 | 0.3 |
| P02743 | Serum amyloid P-component precursor | 3 | 0 | 0 | 1 | 5 | 5 | 4 | 5 | 0.2 |
| P02774 | Vitamin D-binding protein precursor | 37 | 23 | 34 | 31 | 109 | 64 | 75 | 83 | 0.4 |

TABLE 6

Proteins Upregulated in Obese, Diabetic and Hypertensive Female Patients

| Swiss Protein Accession No. | Name of the protein | No of peptide sequencing events found in hypertensive pool | | | Average no of peptide seq. Events | No of peptide sequencing events found in Normal pool | | | Average no of peptide seq. Events | Ratio of averages b/w two pools |
|---|---|---|---|---|---|---|---|---|---|---|
| | | Sample 1 | Sample 2 | Sample 3 | | Sample 1 | Sample 2 | Sample 3 | | |
| P01019 | Angiotensinogen precursor | 18 | 10 | 17 | 15 | 8 | 8 | 5 | 7 | 2.1 |
| P06727 | Apolipoprotein A-IV precursor | 34 | 48 | 34 | 39 | 26 | 14 | 16 | 19 | 2.1 |
| P04114 | Apolipoprotein B-100 precursor | 105 | 92 | 158 | 118 | 45 | 82 | 45 | 57 | 2.1 |

TABLE 6-continued

Proteins Upregulated in Obese, Diabetic and Hypertensive Female Patients

| Swiss Protein Accession No. | Name of the protein | No of peptide sequencing events found in hypertensive pool | | | Average no of peptide seq. Events | No of peptide sequencing events found in Normal pool | | | Average no of peptide seq. Events | Ratio of averages b/w two pools |
|---|---|---|---|---|---|---|---|---|---|---|
| | | Sample 1 | Sample 2 | Sample 3 | | Sample 1 | Sample 2 | Sample 3 | | |
| P02654 | Apolipoprotein C-I precursor | 0 | 10 | 11 | 7 | 0 | 3 | 0 | 1 | 7.0 |
| P02656 | Apolipoprotein C-III precursor | 4 | 9 | 6 | 6 | 2 | 0 | 2 | 1 | 4.8 |
| P01031 | Complement C5 precursor | 7 | 6 | 17 | 10 | 2 | 5 | 6 | 4 | 2.3 |
| P10643 | Complement component C7 precursor | 6 | 0 | 6 | 4 | 0 | 3 | 0 | 1 | 4.0 |
| P05156 | Complement factor I precursor | 8 | 5 | 13 | 9 | 6 | 0 | 7 | 4 | 2.0 |
| P35858 | Insulin-like growth factor binding protein complex acid labile cha | 6 | 3 | 5 | 5 | 0 | 3 | 0 | 1 | 4.7 |
| P51884 | Lumican precursor | 3 | 0 | 5 | 3 | 0 | 0 | 0 | 0 | 2.7 |
| P05155 | Plasma protease C1 inhibitor precursor | 7 | 9 | 11 | 9 | 0 | 4 | 2 | 2 | 4.5 |
| P27169 | Serum paraoxonase/arylesterase 1 | 5 | 8 | 7 | 7 | 0 | 4 | 0 | 1 | 5.0 |
| P25311 | Zinc-alpha-2-glycoprotein precursor | 7 | 7 | 8 | 7 | 0 | 4 | 0 | 1 | 5.5 |

TABLE 7

Proteins Downregulated in Obese, Diabetic, and Hypertensive Female Patients

| Swiss Protein Accession No. | Name of the protein | No of peptide sequencing events found in hypertensive pool | | | Average no of peptide seq. Events | No of peptide sequencing events found in Normal pool | | | Average no of peptide seq. Events | Ratio of averages b/w two pools |
|---|---|---|---|---|---|---|---|---|---|---|
| | | Sample 1 | Sample 2 | Sample 3 | | Sample 1 | Sample 2 | Sample 3 | | |
| P02765 | Alpha-2-HS-glycoprotein precursor | 4 | 3 | 5 | 4 | 21 | 20 | 17 | 19 | 0.2 |
| P02652 | Apolipoprotein A-II precursor | 0 | 12 | 14 | 9 | 69 | 20 | 30 | 40 | 0.2 |
| P05090 | Apolipoprotein D precursor | 0 | 2 | 6 | 3 | 9 | 2 | 8 | 6 | 0.4 |
| P02649 | Apolipoprotein E precursor | 8 | 10 | 8 | 9 | 24 | 3 | 40 | 22 | 0.4 |
| O95445 | Apolipoprotein M | 2 | 0 | 6 | 3 | 7 | 3 | 6 | 5 | 0.5 |
| O95445 | Apolipoprotein-L1 precursor | 0 | 2 | 5 | 2 | 4 | 5 | 7 | 5 | 0.4 |
| P02749 | Beta-2-glycoprotein I precursor | 27 | 22 | 36 | 28 | 64 | 63 | 59 | 62 | 0.5 |
| Q96IY4 | Carboxypeptidase B2 precursor | 0 | 0 | 0 | 0 | 2 | 0 | 2 | 1 | 0.0 |
| P07357 | Complement component C8 alpha chain precursor | 2 | 2 | 4 | 3 | 7 | 8 | 9 | 8 | 0.3 |
| P07358 | Complement component C8 beta chain precursor | 4 | 4 | 0 | 3 | 6 | 8 | 5 | 6 | 0.4 |
| P07360 | Complement component C8 gamma chain precursor | 0 | 0 | 3 | 1 | 4 | 4 | 4 | 4 | 0.3 |
| Q03591 | Complement factor H-related protein 1 precursor | 0 | 0 | 0 | 0 | 3 | 7 | 0 | 3 | 0.0 |
| P00739 | Haptoglobin-related protein precursor | 0 | 0 | 0 | 0 | 16 | 22 | 0 | 13 | 0.0 |
| Q96PD5 | N-acetylmuramoyl-L-alanine amidase precursor | 3 | 0 | 0 | 1 | 4 | 8 | 4 | 5 | 0.2 |
| P00747 | Plasminogen precursor | 0 | 0 | 0 | 0 | 8 | 6 | 7 | 7 | 0.0 |
| P02775 | Platelet basic protein precursor | 0 | 0 | 0 | 0 | 0 | 3 | 3 | 2 | 0.0 |
| P02787 | Serotransferrin precursor | 38 | 43 | 45 | 42 | 102 | 98 | 78 | 93 | 0.5 |
| P35542 | Serum amyloid A-4 protein precursor | 4 | 8 | 0 | 4 | 13 | 4 | 10 | 9 | 0.4 |
| P05452 | Tetranectin precursor | 0 | 0 | 0 | 0 | 4 | 6 | 3 | 4 | 0.0 |
| P02774 | Vitamin D-binding protein precursor | 29 | 33 | 43 | 35 | 109 | 64 | 75 | 83 | 0.4 |

As an initial screen, the spectral count (number of peptide sequencing events) was averaged. Based on these results, a further study was performed of selected proteins by peak area quantitation, as described above.

Figure 4:
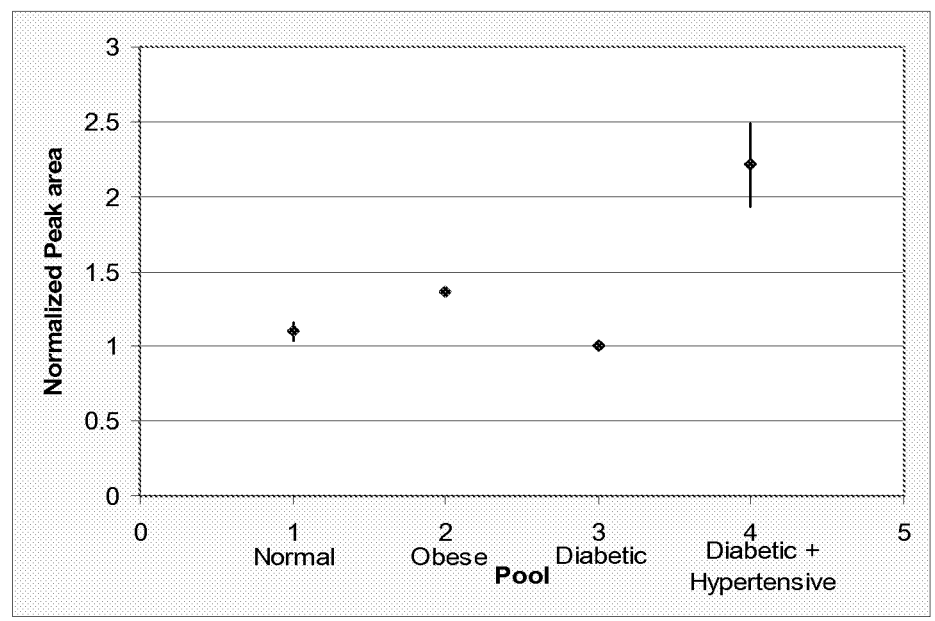
FIG. 4 is a graphic representation of the relative protein concentrations of angiotensinogen in plasma samples from various patient groups.

Based on the results described herein, angiotensinogen was identified as a biomarker for hypertension. Angiotensinogen is the precursor of biologically active angiotensin I and II. The renin-angiotensinogen system plays a role in the regulation of extracellular fluid volume and blood pressure in the body. To determine the relative abundance of angiotensinogen in the various sample pools, the following two angiotensinogen peptides were quantified by peak area measurements. The peptide R.SLDFTELDVAAEK.I (SEQ ID NO:1) (with a +2 charge, a precursor ion mass of 720.4 amu, and a retention time of 95.1 min) and the peptide K.ALQDQLVLVAAK.L (SEQ ID NO:2) (with a +2 charge, a precursor ion mass of 635.5 amu, and a retention time of 87.8 min) were quantitated. As shown in FIG. 4, angiotensinogen was overexpressed in hypertensive patients and was also slightly elevated in obese patients compared to the normal pool.

Apolipoprotein (Apo) C1 is a 6.6-kDa protein present in plasma and associated with lipoproteins. ApoC1 is an inhibitor of lipoprotein binding to the LDL receptor, LDL receptor-related protein, and the VLDL receptor. It also is the major plasma inhibitor of cholesteryl ester transfer protein, and may interfere directly with fatty acid uptake.

Based on the results described herein, apolipoprotein C1 was identified as a biomarker for diabetes, obesity, and hypertension. To determine the relative abundance of apolipoprotein C1 in the various sample pools, the following two apolipoprotein C1 peptides were quantified by peak area measurements: the peptide K.MREWFSETFQK.V (SEQ ID NO:3) (with a +2 charge, a precursor ion mass of 745.49 amu, and a retention time of 85.6 min) and the peptide R.EWFSETFQK.V (SEQ ID NO:4) (with a +2 charge, a precursor ion mass of 602.2 amu, and a retention time of 90.5 min) were quantitated.

Figure 5:
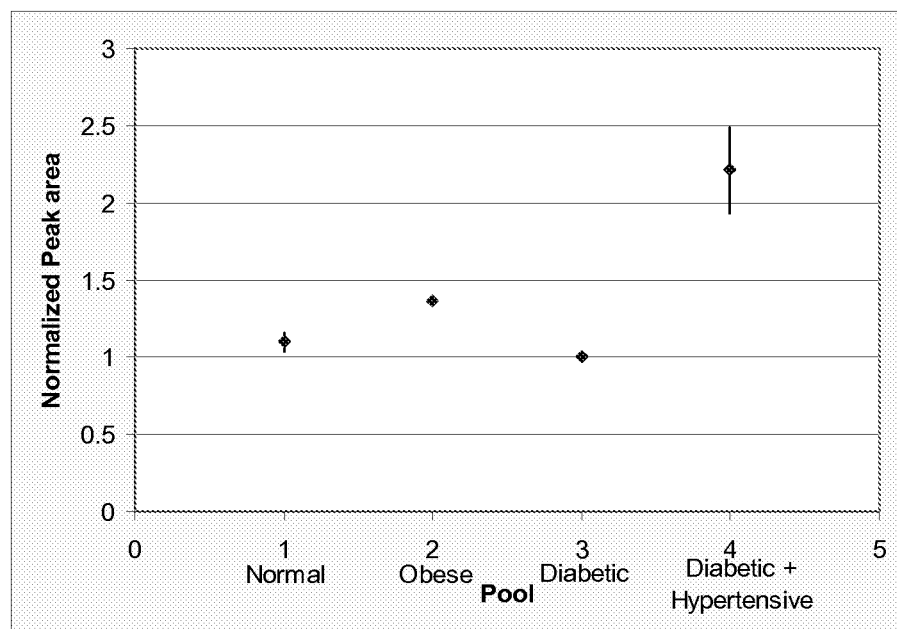
FIG. 5 is a graphic representation of the relative protein concentrations of apolipoprotein C1 in plasma samples from various patient groups.

As shown in FIG. 5, apolipoprotein C1 was present at high levels in plasma in obese, diabetic and hypertensive patients.

In the results described herein, the increase of Apo C1 was mirrored in the levels of related apolipoprotein CIII and apolipoprotein B, as well as insulin-like growth factor (IgF) binding protein.

The results described herein demonstrate that by using a combination of six protein depletion and multi-lectin affinity chromatography, the complexity of the human plasma proteome can be reduced to allow identification of protein biomarkers for disease studies by proteomic analysis. With the use of the two column approach, the non-glycoprotein fraction was depleted in terms of both the major plasma protein albumin as well as glycoproteins of high abundance such as alpha-2-macroglobulin. The utility of this approach to a disease study by the identification of proteins such as angiotensinogen and apolipoprotein C1, which were shown to be present at higher levels in obese, diabetic and hypertensive patients, was demonstrated.

Example 2

Reversal of Differential Expression of Proteins in Diabetic Subjects Following Gastric Bypass Surgery Protocol 24 Caucasian women are used in this study: 8 diabetics (18-55 years of age, BMI of 35-50, 3 blood samples each—24 total); 8 euglycemic (18-55 years of age, BMI of 35-50, 3 blood sample each—24 total); and 8 "normal" controls (lean and euglycemic, 1 sample each—8 total). Plasma samples are obtained from each patient and the samples are analyzed as described in Example 1. The patients then undergo routine gastric bypass surgery, e.g., silastic ring Roux-en-Y gastric bypass or a Fobi pouch operation. After the surgery, plasma samples are obtained from each patient 6 days, 1 month, 3 months, and 6 months following the surgery. On the morning of the surgery and 6 days later, a short intravenous glucose tolerance test is performed on each patient, and insulin resistance is measured on the morning of surgery, 6 days later, and again at 3, 6, 9, and 12 months after surgery (see, e.g., Wickremesekera et al., *Obesity Surgery* (2005) 15:474-481).

The samples are then analyzed as described in Example 1. Briefly, the six most abundant proteins are depleted using MARS, glycosylated proteins are separated from nonglycosylated proteins by M-LAC, nonglycosylated proteins are subjected to tryptic digestion, and the tryptic digests are analyzed by nano LC-MS/MS.

Results

Proteins are identified that are differentially expressed between diabetic and control patients before gastric bypass surgery. These include angiotensinogen and apolipoprotein C1. Following gastric bypass surgery, insulin resistance is improved in the diabetic patients, which is correlated with changes in the levels of proteins, identified as differentially expressed in diabetic patients before surgery (including angiotensinogen and apolipoprotein C1), to about the same levels measured in control patients.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of identifying a subject having, or at risk of developing obesity, and/or hypertension, the method comprising:
   determining the level of angiotensinogen or apolipoprotein C1 (i) in a test biological sample obtained from the subject and (ii) in a control biological sample of like tissue derivation from a control subject not having, or at risk of developing, obesity, and/or hypertension wherein the step of determining the level of angiotensinogen or apolipoprotein C1 in the test plasma sample and in the control plasma sample comprises:
      immuno-depleting albumin, IgG, IgA, transferrin, antitrypsin, and haptoglobin (i) from the test plasma sample, resulting in a depleted test plasma sample, and (ii) from the control plasma sample, resulting in a depleted control plasma sample;
      separating (i) the depleted test plasma sample into a first fraction comprising glycosylated polypeptides and a second fraction comprising nonglycosylated polypeptides, and (ii) the depleted control plasma sample into a third fraction comprising glycosylated polypeptides and a fourth fraction comprising non-glycosylated polypeptides;
      digesting with trypsin (i) the non-glycosylated polypeptides in the second fraction, resulting in a test tryptic digest, and (ii) the non-glycosylated polypeptides in the fourth fraction, resulting in a control tryptic digest;
      subjecting to liquid chromatography-mass spectrometry (LC/MS) (i) the test tryptic digest, resulting in a test polypeptide profile, and (ii) the control tryptic digest, resulting in a control polypeptide profile; and
   comparing the level of angiotensinogen or apolipoprotein C1 in the test sample and in the control sample, wherein an increased level of angiotensinogen or apolipoprotein C1 in the test sample relative to the control sample is indicative that the subject has, or is at risk of developing obesity, and/or hypertension.

2. The method of claim 1, wherein the test and the control biological samples are plasma samples.

3. The method of claim 1, wherein the step of immuno-depleting the samples comprises a multiple affinity removal system.

4. The method of claim 1, wherein the step of separating the depleted samples comprises using a multi-lectin column.

5. The method of claim 1, wherein the LC/MS comprises reversed phase chromatography.

6. A method of determining the level of angiotensinogen or apolipoprotein C1 in a test plasma sample relative to a control plasma sample, the method comprising:
- obtaining a test plasma sample from a test subject and a control plasma sample from a control subject;
- immuno-depleting albumin, IgG, IgA, transferrin, antitrypsin, and haptoglobin (i) from the test plasma sample, resulting in a depleted test plasma sample, and (ii) from the control plasma sample, resulting in a depleted control plasma sample;
- separating (i) the depleted test plasma sample into a first fraction comprising glycosylated polypeptides and a second fraction comprising non-glycosylated polypeptides, and (ii) the depleted control plasma sample into a third fraction comprising glycosylated polypeptides and a fourth fraction comprising non-glycosylated polypeptides;
- digesting with trypsin (i) the non-glycosylated polypeptides in the second fraction, resulting in a test tryptic digest, and (ii) the non-glycosylated polypeptides in the fourth fraction, resulting in a control tryptic digest;
- subjecting to liquid chromatography-mass spectrometry (LC/MS) (i) the test tryptic digest, resulting in a test polypeptide profile, and (ii) the control tryptic digest, resulting in a control polypeptide profile; and
- comparing the level of angiotensinogen or apolipoprotein C1 in the test polypeptide profile to the level of angiotensinogen or apolipoprotein C1 in the control polypeptide profile.

7. The method of claim 6, wherein the step of immuno-depleting the samples comprises a multiple affinity removal system.

8. The method of claim 6, wherein the step of separating the depleted samples comprises using a multi-lectin column.

9. The method of claim 6, wherein the LC/MS comprises reversed phase chromatography.

10. The method of claim 6, wherein a level of angiotensinogen or apolipoprotein C1 in the test plasma sample that is different relative to the control plasma sample is indicative that the test subject has, or is at risk of developing, diabetes, obesity, and/or hypertension.

11. A method of identifying a biomarker for diabetes, obesity, and/or hypertension, the method comprising:
- obtaining a test plasma sample from a subject having or at risk of developing diabetes, obesity, and/or hypertension, and obtaining a control plasma sample from a subject not having or not at risk of developing diabetes, obesity, and/or hypertension;
- immuno-depleting albumin, IgG, IgA, transferrin, antitrypsin, and haptoglobin from the test and control samples, resulting in a depleted test sample and a depleted control sample;
- separating the depleted test sample into a first fraction comprising test glycosylated polypeptides and a second fraction comprising test non-glycosylated polypeptides, and separating the depleted control sample into a third fraction comprising control glycosylated polypeptides and a fourth fraction comprising control non-glycosylated polypeptides;
- independently digesting the test non-glycosylated polypeptides in the second fraction and the control non-glycosylated polypeptides in the fourth fraction with trypsin, resulting in a test tryptic digest and a control tryptic digest; independently subjecting the test tryptic digest and the control tryptic to LC/MS, resulting in a test polypeptide profile and a control polypeptide profile; and
- comparing the test polypeptide profile and the control polypeptide profile,
- a polypeptide present at a level in the test polypeptide profile that is different than in the control polypeptide profile being indicative of the polypeptide as a biomarker for diabetes, obesity, and/or hypertension.

12. The method of claim 11, wherein the step of immuno-depleting the samples comprises a multiple affinity removal system.

13. The method of claim 11, wherein the step of separating the depleted samples comprises using a multi-lectin column.

14. The method of claim 11, wherein the LC/MS comprises reversed phase chromatography.

15. A method of identifying a subject having, or at risk of developing obesity and/or comorbid diabetes and hypertension, the method comprising:
- determining the level of angiotensinogen or apolipoprotein C1 (i) in a test plasma sample obtained from the subject and (ii) in a control plasma sample of like tissue derivation from a control subject not having, or at risk of developing, diabetes, obesity, and/or hypertension wherein the step of determining the level of angiotensinogen or apolipoprotein C1 in the test plasma sample and in the control plasma sample comprises:
  - immuno-depleting albumin, IgG, IgA, transferrin, antitrypsin, and haptoglobin (i) from the test plasma sample, resulting in a depleted test plasma sample, and (ii) from the control plasma sample, resulting in a depleted control plasma sample;
  - separating (i) the depleted test plasma sample into a first fraction comprising glycosylated polypeptides and a second fraction comprising non-glycosylated polypeptides, and (ii) the depleted control plasma sample into a third fraction comprising glycosylated polypeptides and a fourth fraction comprising non-glycosylated polypeptides;
  - digesting with trypsin (i) the non-glycosylated polypeptides in the second fraction, resulting in a test tryptic digest, and (ii) the non-glycosylated polypeptides in the fourth fraction, resulting in a control tryptic digest;
  - and subjecting to liquid chromatography-mass spectrometry (LC/MS) (i) the test tryptic digest, resulting in a test polypeptide profile, and (ii) the control tryptic digest, resulting in a control polypeptide profile; and
- comparing the level of angiotensinogen or apolipoprotein C1 in the test sample and in the control sample, wherein an increased level of angiotensinogen or apolipoprotein C1 in the test sample relative to the control sample being indicative that the subject has, or is at risk of developing obesity and/or comorbid diabetes and hypertension.

* * * * *

UNITED STATES PATENT AND TRADEMARK OFFICE
CERTIFICATE OF CORRECTION

PATENT NO. : 8,628,912 B2  Page 1 of 1
APPLICATION NO. : 12/667456
DATED : January 14, 2014
INVENTOR(S) : Hancock et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 963 days.

Signed and Sealed this
Twenty-second Day of September, 2015

Michelle K. Lee
*Director of the United States Patent and Trademark Office*